(12) United States Patent
Atlas et al.

(10) Patent No.: US 6,420,429 B1
(45) Date of Patent: *Jul. 16, 2002

(54) BRAIN TARGETED LOW MOLECULAR WEIGHT HYDROPHOBIC ANTIOXIDANT COMPOUNDS

(75) Inventors: Daphne Atlas, Jerusalem; Eldad Melamed, Tel Aviv; Daniel Offen, Kfar Ha'Roe, all of (IL)

(73) Assignees: Yissum Research Development Company of the Hebrew University of Jerusalem, Jerusalem; Ramot University Authority for Applied Research & Industrial Development Ltd., Tel Aviv; MOR-Research Applications Ltd., Petah Tikva, all of (IL)

( * ) Notice: Subject to any disclaimer, the term of this patent is extended or adjusted under 35 U.S.C. 154(b) by 0 days.

This patent is subject to a terminal disclaimer.

(21) Appl. No.: 09/322,980

(22) Filed: Jun. 1, 1999

Related U.S. Application Data

(63) Continuation-in-part of application No. PCT/US97/23997, filed on Dec. 23, 1997.

(51) Int. Cl.⁷ ...................... A61K 31/165; C07C 321/00
(52) U.S. Cl. ..................... 514/625; 514/2; 514/544; 514/550; 514/562; 514/613; 560/147; 562/556; 564/152
(58) Field of Search ............... 514/2, 547, 550, 514/562, 613, 625; 560/147; 562/556; 564/152

(56) References Cited

U.S. PATENT DOCUMENTS

| | | | | |
|---|---|---|---|---|
| 5,464,825 A | * | 11/1995 | Anderson et al. | 514/18 |
| 5,736,565 A | * | 4/1998 | Ferrari | 514/423 |
| 5,762,922 A | * | 6/1998 | Noble et al. | 424/85.1 |
| 5,874,468 A | * | 2/1999 | Atlas et al. | 514/547 |

OTHER PUBLICATIONS

Anderson et al., Analy. Biochem. vol. 183(1) pp. 16–20 (11/89).*

CAPLUS AN 1995:720776 to Heap et al., Biochem. Pharmacol. vol. 50(2) pp. 263–270.*

* cited by examiner

*Primary Examiner*—Bennett Celsa
(74) *Attorney, Agent, or Firm*—G. E. Ehrlich Ltd.

(57) ABSTRACT

Novel brain targeted low molecular weight, hydrophobic antioxidants and use of antioxidants in treatment of central nervous system neurodegenerative disorders such as Parkinson's, Alzheimer's and Creutzfeldt-Jakob's diseases and in treatment of conditions of peripheral tissues, such as acute respiratory distress syndrome, amyotrophic lateral sclerosis, atherosclerotic cardiovascular disease and multiple organ dysfunction, in which oxidants are overproduced.

8 Claims, 6 Drawing Sheets

BRAIN TARGETED LOW MOLECULAR WEIGHT HYDROPHOBIC ANTIOXIDANT COMPOUNDS

This is a continuation-in-part of PCT/US97/23997, filed Dec. 23, 1997.

FIELD AND BACKGROUND OF THE INVENTION

The present invention relates to composition and use of novel antioxidant compounds, also referred herein as antioxidants. More particularly, the present invention relates to novel brain targeted low molecular weight, hydrophobic antioxidants and their use in treatment of central nervous system neurodegenerative disorders such as Parkinson's, Alzheimer's and Creutzfeldt-Jakob's diseases. The compounds according to the present invention can also be used as antioxidants in treating conditions of peripheral tissues, such as acute respiratory distress syndrome, amyotrophic lateral sclerosis, atherosclerotic cardiovascular disease and multiple organ dysfunction.

Correlation Between Oxidative Stress and Various Neurodegenerative Pathologies.

In the last few years evidences have accumulated which connect oxidative stress (OS) with the pathogenesis of Parkinson's, Alzheimer's Creutzfeldt-Jakob's diseases and other human neurodegenerative disorders (Olanow, 1990, 1993; Fahn and Cohen, 1992; Cafe et al., 1996, Brown et al., 1996; Thomas et al., 1996).

These studies were initiated (i) since outo-oxidation of levodopa and dopamine is known to produce oxygen free radicals, $H_2O_2$, quinones and semiquinones, the later two are high molecular weight polymers possessing an aromatic structure and are therefore potentially toxic and (ii) since post-mortem studies in Parkinson's disease patients showed a dramatic decline in the levels of endogenous reduced glutathione (GSH), which is, as is further delineated hereinbelow, essential for maintaining the oxidative state of the cells. The decrease in reduced glutathione levels progresses from the pre symptomatic Parkinson's disease condition to the advanced clinical Parkinson's disease condition.

Two possible explanations may account for the role played by oxidative stress in the pathogenesis of Parkinson's disease.

According to a first hypothesis it is assumed that cells of the substantia nigra (SN), are constantly under oxidative stress due to the oxidation of the catechol ring of dopamine. Dopamine, like other catecholamines, undergoes spontaneous oxidation to form semiquinones, oxygen free-radicals and $H_2O_2$ as metabolic by-products. In addition, one of the disposal routs for dopamine is its enzymatic oxidation by MAO (monamine oxidase) type A or B which, like the spontaneous oxidation, creates semiquinones, oxygen free radicals and $H_2O_2$.

These products may cause accumulative oxidation damage within the substantia nigra cells, and eventually lead to cell death. Non-affected cells increase the turnover of dopamine, which in turn, generates more toxic free radicals. Indeed, it was shown that in the presence of $H_2O_2$ and copper ions, dopamine as well as L-dopa (levodopa) cause oxidative damage to DNA (Jenner 1994; Spencer et al., 1994).

According to another hypothesis it is assumed that Parkinson's disease is caused by a substance of an unknown composition, similar to the toxin 1-methyl-4-phenyl-1,2,3,6-tetrahydropyridine (MPTP), which is enzymatically converted to the toxic metabolite 1-methyl-4-phenyl pyridine (MPP$^+$) by MAO type B. Since this reaction releases free oxygen radicals, thereby increasing the oxidative stress imposed on the cells, similar mechanisms might affect the nigral cells in Parkinson's disease. If this type of a process indeed occurs in Parkinsonian brains, than again, it would create a high level of oxidative stress in the dopaminergic cells at the substantia nigra.

The following findings demonstrate a strong indication for oxidative stress as a possible cause for the pathogenesis of Parkinson's disease.

First, the iron content in the substentia Nigra of Parkinson's disease patients was found to be significantly higher while ferritin content, the protein which bind free iron ions within tissues, was found to be significantly lower then normal values (Olanow 1990; 1993 and Jenner 1994). These two phenomena indicate a situation where the amount of free iron which acts as a catalyst in oxidation reactions, is abnormally high and thus may contribute to the speed of oxidation reactions at the substantia nigra of Parkinson's disease patients. The above indication was given support when it was shown that injection of free iron directly into the substantia nigra of rodents caused the appearance of Parkinsonian symptoms, which symptoms could be overcome by addition of transferrin, the protein which binds free iron in the blood plasma (Jenner 1994).

Second, one of the protective mechanisms against oxidation processes in the brain is reduced glutathione (GSH), which upon oxidation to oxidized glutathione (GS), acts as a reducing agent. In the substantia nigra of Parkinson's disease patients the level of reduced glutathione is significantly low, whereas the level of oxidized glutathione remains normal. Hence the oxidation potential in the substantia nigra of Parkinson's disease patients is low. This change in the level of reduced glutathione is in all likelihood, specific for Parkinson's disease. The oxidation products which are formed during spontaneous and enzymatic oxidation of dopamine, as described hereinabove, lower the level of reduced glutathione, and thereby increase the ratio of oxidized/reduced glutathione. Since the level of γ-glutamyl-cysteine synthetase, the enzyme which is a rate limiting enzyme in the biochemical pathway of glutathione synthesis, is normal, the ratio stays high and induces a state of oxidative stress in the cells. It is interesting that the level of the enzyme which is responsible for the removal of oxidized glutathione, γ-glutamyl transpeptidase in the cells is higher, as if the cells attempt to overcome the increased oxidative stress by trying to get rid of oxidized glutathione (Sian et al., 1994).

Third, additional evidence for the abnormally high oxidative stress in the Parkinsonian brain comes from a study of lipid oxidation products in the substantia nigra of Parkinson's disease patients. In general, the level of unsaturated fatty acids is low in the substantia nigra, however, the level of lipid hydroperoxides which are the oxidation products of unsaturated fatty acids is high in the substantia nigra of Parkinson's patients. This finding indicates the presence of an abnormally higher frequency of oxidation processes in the Parkinsonian substantia nigra (Jenner, 1994).

And finally, one of the animal models which are currently used for the study of Parkinson's disease is created by the injection of 6-hydroxy-dopamine. Like dopamine, this false neurotransmitter elevates the level of the oxidation products during its degradation, thus leading to cell death. Since the biological half life of 6-hydroxy-dopamine is much longer and since it is readily taken-up by the cells, it increases the rate by which the animal develops the symptoms of the disease.

The different pathological makers of various neurodegenerative diseases e.g., Lewy bodies, plaques, etc., indicate different causal factors in the initiation of these diseases. However, there is growing evidence that once initiated, the progression of a large number of neurodegenerative diseases, is quite similar.

Although the characteristic symptoms are descriptive for each neurodegenerative disease, it appears that elevation of the oxidative state of the cells at specific regions in the brain is an important factor in the etiology of Parkinson's disease, basal ganglia degenerative diseases, motoneuron diseases, Alzheimer's and also the Creutzfeldt-Jakob's disease.

An indication for a role played by oxidative stress in the pathogenesis of Alzheimer's disease was found while in a recent study, the relationship between the β-amyloid protein fragments and oxygen radical formation was tested in a system that is highly sensitive and responds to free oxygen radicals. This system utilizes the vasoactivity of the blood vessel which, in the presence of β-amyloid, enhances the phenylephrine mediated contraction of the vessels. Pre treatment of the blood vessel with superoxide dismutase (SOD), an enzyme that scavenges free oxygen radicals, eliminated the effect of β-amyloid, namely, there was no enhancement of vasoconstriction. Whereas, if SOD was added after treatment with β-amyloid protein, the protective effect of the radical scavenger was abolished (Thomas et al., 1996). Recently, other studies have shown that oxidative stress and free radicals production are linked to β-amyloid fragment which includes amino acids 25–35 and may contribute to neurodegenerative events associated with Alzheimer's disease (Cafe et al., 1996).

Possible indications for a role played by oxidative stress in the pathogenesis of Scrapie, spongyform encephalopathy (BSE) and Creutzfeldt-Jakob's diseases are listed hereinbelow.

In a recent study, it was demonstrated that the toxic effect of Scrapie requires the presence of microglia cells which respond to a prion protein fragment (PrP106-126) by increasing their oxygen radical production. Interestingly, all these effects were absolutely dependent on mice that express the prion protein $PrP^c$ (Brown et al., 1996). The contribution of progressive oxidative stress to the state of various diseases and to mechanism of cell death is further demonstrated in a study by P. Jenner in The Lancet (1994) 344, 796–798, which is incorporated by reference as if fully set forth herein.

New Therapeutic Aspects.

The use of glial cell-derived neurotrophic factor (GDNF) was established as a potential stimulant for the increase of dopamine levels in midbrain of rhesus monkeys (Gash et al., 1996). This study which extends previous results obtained with rodents, is promising as a potential treatment for Parkinson's disease. However, like any other protein, GDNF cannot cross the blood brain barrier. Therefore, it can not be taken orally or be injected systemically. The only possible mode of administration would thus be via an intracerebral injection which would constitute a main drawback for such a treatment.

Similarly, in other neurodegenerative diseases such as Alzheimer's and Creutzfeldt-Jakob's, where the theory of free oxygen radicals appears to play a major role, there is no major breakthrough in therapy.

To overcome high oxidative stress it would be beneficial to augment the reduced state of the cells at the central nervous system (CNS). One of the possible ways to do it is by increasing the level of reduced glutathione or other scavengers of free radicals and free oxygen in the brain.

In general, in order to lower oxidative stress levels, various antioxidants are being used. The most common are vitamin E and vitamin C. However, vitamin E was found to be ineffective at decreasing the oxidative stress at the substantia nigra (The Parkinson Study Group, 1993, Offen et al., 1996) since this compound, although capable of crossing the blood brain barrier, is trapped in the cell membrane and therefore does not reach the cytoplasm where its antioxidant properties are needed. Vitamin C does not cross the blood brain barrier and therefore, cannot be used effectively for neurodegenerative diseases of central origin.

Recently, a similar approach for reducing the levels of free oxygen, was taken for the treatment of asthma (Bundy et al., 1995). A reactive oxygen inhibitor was synthesized (2,4-diaminopyrrolo-[2,3-d]pyrimidines) and after a successful pharmacological bio-availability and toxicity tests was selected for clinical evaluation.

A somewhat different approach involves stimulating the production of endogenous antioxidants, especially reduced glutathione. To this end a drug known as Procysteine which boosts cellular production of glutathione by loading the cells with cysteine is under clinical trials these days by Free Radical Sciences Inc. (CA, US) to treat conditions of acute respiratory distress syndrome (ARDS) which includes overproduction of oxidants or reactive oxygen species by the immune system. Other conditions in which overproduction of oxidants is experienced include but are not limited to amyotrophic lateral sclerosis, atheroscierotic cardiovascular disease and multiple organ dysfunction. See, for example, Charles Craig, 1996.

There is thus a widely recognized need for, and it would be highly advantageous to have novel antioxidant compounds and methods for use of antioxidants in treatment of central nervous system neurodegenerative disorders such as Parkinson's, Alzheimer's and Creutzfeldt-Jakob's diseases and in treating conditions of peripheral tissues, such as acute respiratory distress syndrome, amyotrophic lateral sclerosis, atheroscierotic cardiovascular disease and multiple organ dysfunction, which compounds act as oxygen scavengers to lower the oxidative stress within and in the vicinity of affected cells and eventually to stop cell death which is associated with oxidative stress in the brain and/or peripheral tissues.

SUMMARY OF THE INVENTION

According to the present invention there are provided brain and/or peripheral tissues targeted, low molecular weight, hydrophobic antioxidant compounds. Further provided are methods of using same for treatment of various etiologies. Particularly, these etiologies are neurodegenerative disorders, in which disorders pathology in the brain is associated with oxidative stress.

According to further features in preferred embodiments of the invention described below provided is a compound selected from the group consisting of

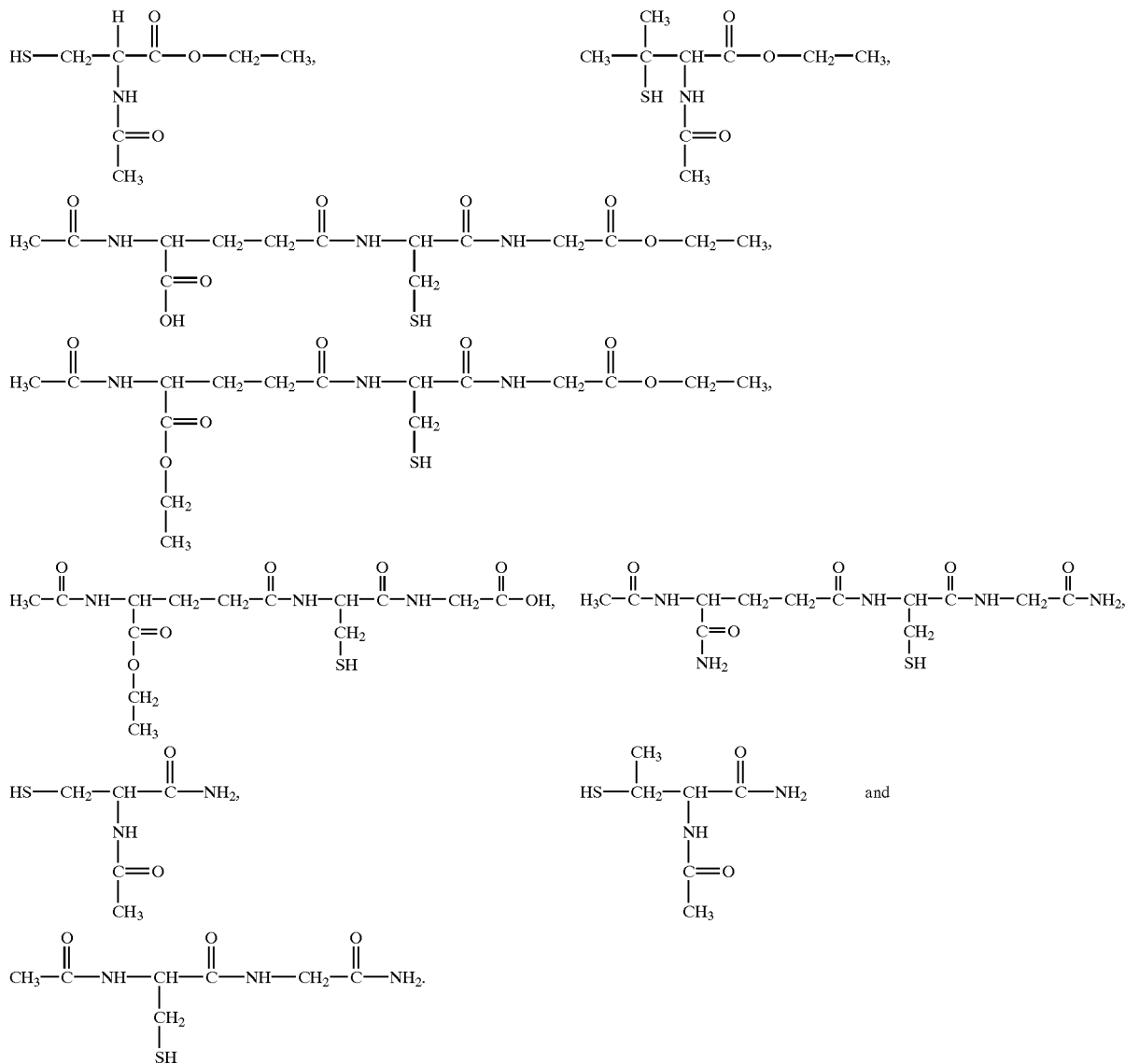

According to further features in preferred embodiments of the invention described below provided is a method of preparing N-acetyl cysteine ethyl ester, which is the first compound above, the method comprising the steps of (a) mixing N-acetyl cysteine with a cooled solution of thionyl chloride and absolute ethanol; (b) refluxing the mixture; and (c) removing volatiles from the mixture for obtaining a first residue.

According to still further features in the described preferred embodiments the method further comprising the steps of (d) dissolving the first residue in water; and (e) extracting the first residue from the water with methylene chloride.

According to still further features in the described preferred embodiments the method further comprising the step of (f) drying the extract for obtaining a second residue.

According to still further features in the described preferred embodiments the method further comprising the step of (g) crystallizing the second residue from petroleum ether.

According to further features in preferred embodiments of the invention described below provided is a method of preparing N-acetyl β,β-dimethyl cysteine ethyl ester, which is the second compound above, the method comprising the steps of (a) mixing N-acetyl β,β-dimethyl cysteine with a cooled solution of thionyl chloride and absolute ethanol; (b) refluxing the mixture; and (c) removing volatiles from the mixture for obtaining a first residue.

According to still further features in the described preferred embodiments the method further comprising the steps of (d) dissolving the first residue in water; and (e) extracting the first residue from the water with methylene chloride.

According to still further features in the described preferred embodiments the method further comprising the step of (f) drying the extract for obtaining a second residue.

According to still further features in the described preferred embodiments the method further comprising the step of (g) crystallizing the second residue from a methanol water solution.

According to further features in preferred embodiments of the invention described below provided is a method of preparing N-acetyl glutathione amide, which is the ninth compound above, the method comprising the steps of (a) bobbling ammonia gas through cooled ethanol; (b) adding N-acetyl glutathione ethyl ester, which is the seventh compound above; (c) sealing a container holding the reaction; and (d) removing access ammonia and ethanol.

According to further features in preferred embodiments of the invention described below provided is a method of preparing N-acetyl cysteine amide, which is the tenth compound above, the method comprising the steps of (a) bobbling ammonia gas through cooled ethanol; (b) adding N-acetyl cysteine ethyl ester, which is the first compound above; (c) sealing a container holding the reaction; and (d) removing access ammonia and ethanol.

According to further features in preferred embodiments of the invention described below provided is a method of preparing N-acetyl β,β dimethyl cysteine amide, which is the eleventh compound above, the method comprising the steps of (a) bobbling ammonia gas through cooled ethanol; (b) adding N-acetyl β,β dimethyl cysteine ethyl ester, which is the second compound above; (c) sealing a container holding the reaction; and (d) removing access ammonia and ethanol.

According to further features in preferred embodiments of the invention described below provided is a method of reducing oxidative stress in the brain of an organism having a blood brain barrier, the method comprising the step of administering a compound to the organism, the compound having (a) a combination of molecular weight and membrane miscibility properties for permitting the compound to cross the blood brain barrier of the organism; (b) a readily oxidizable chemical group for exerting antioxidation properties; and (c) a chemical make-up for permitting the compound or its intracellular derivative to accumulate within the cytoplasm of cells.

According to still further features in the described preferred embodiments the readily oxidizable chemical group is a sulfhydril group.

According to still further features in the described preferred embodiments the chemical make-up is selected having an ester moiety which is removable by hydrolysis imposed by intracellular esterases.

According to still further features in the described preferred embodiments the administration is peripheral (i.e., not directly to the central nervous system, e.g., orally or by intravenous injection).

According to still further features in the described preferred embodiments the ester moiety is selected from the group consisting of alkyl ester and aryl ester.

According to still further features in the described preferred embodiments the alkyl and aryl esters are selected from the group consisting of methyl ester, ethyl ester, hydroxyethyl ester, t-butyl ester, cholesteryl ester, isopropyl ester and glyceryl ester.

According to still further features in the described preferred embodiments the organism is a human being.

According to still further features in the described preferred embodiments the oxidative stress in the brain is a pathology caused by a neurodegenerative disorder.

According to still further features in the described preferred embodiments the neurodegenerative disorder is selected from the group consisting of Parkinson's disease, Alzheimer's disease, basal ganglia degenerative diseases, motoneuron diseases, Scrapie, spongyform encephalopathy and Creutzfeldt-Jakob's disease.

According to further features in preferred embodiments of the invention described below provided is a method of reducing oxidative stress in a tissues of an organism, the method comprising the step of administering a compound to the organism, the compound is selected from the group consisting of

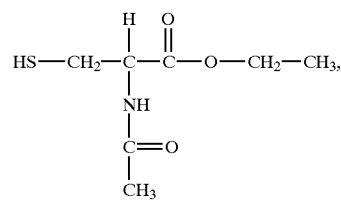

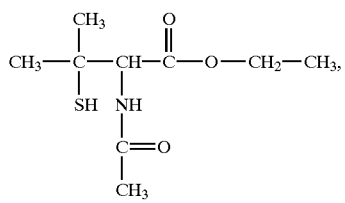

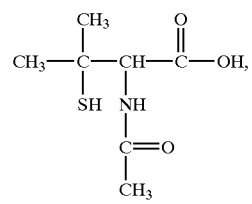

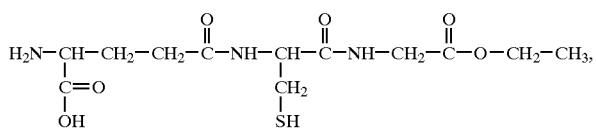

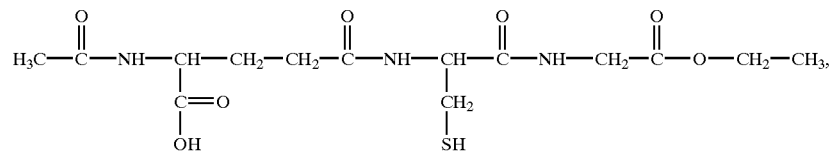

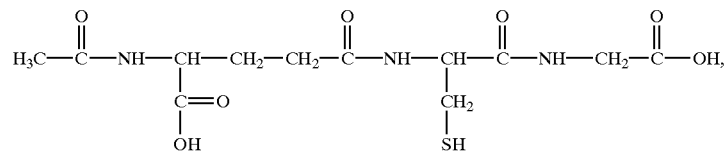

-continued

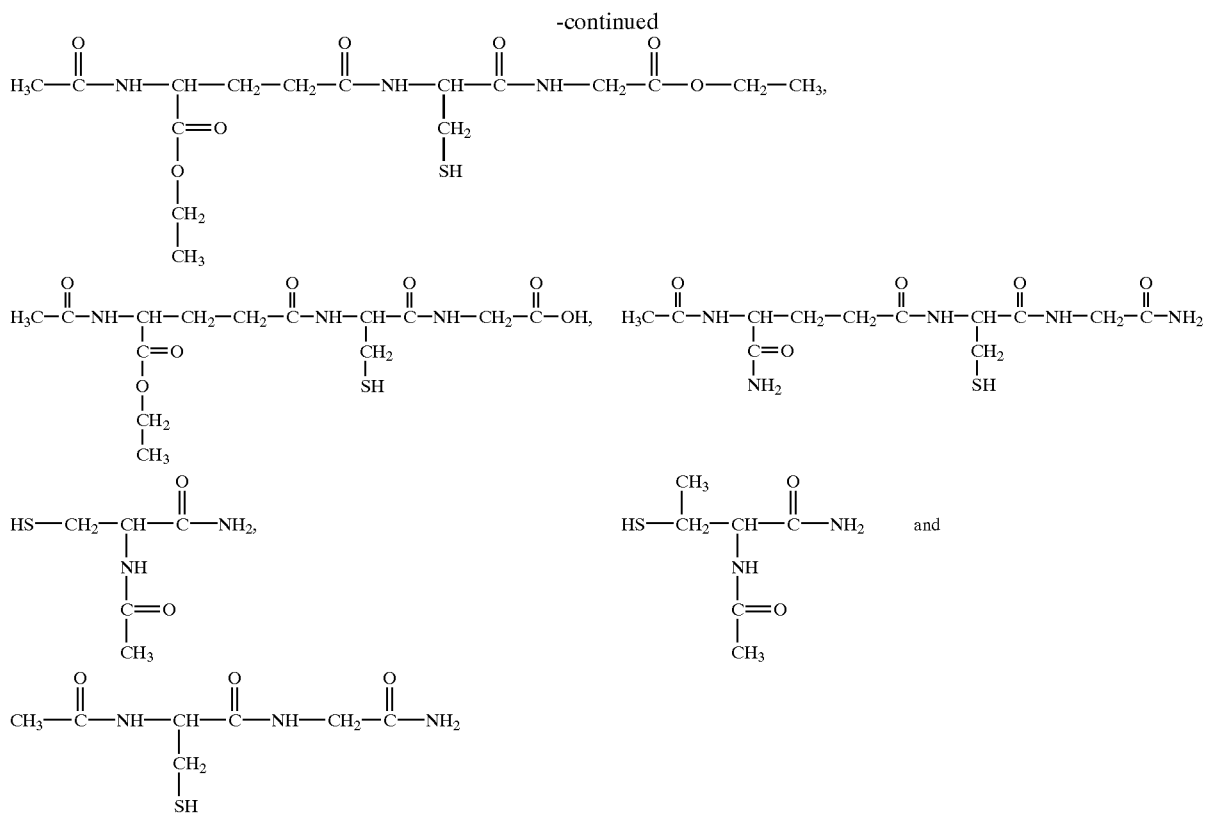

According to further features in preferred embodiments of the invention described below provided is a method of reducing or abolishing, extracellular or intracellular, natural or induced oxidation effects imposed on cells, the method comprising the step of subjecting the cells to a compound selected from the group consisting of N-acetyl cysteine ethyl ester, β,β-dimethyl cysteine ethyl ester, N-acetyl-β,β-dimethyl cysteine, glutathione ethyl ester, N-acetyl glutathione ethyl ester, N-acetyl glutathione, N-acetyl (α ethyl ester) glutathione, N-acetyl (α ethyl ester) glutathione ethyl ester, N-acetyl glutathione amide, N-acetyl cysteine amide, N-acetyl β,β dimethyl cysteine amide and N-acetyl cysteine glycine amide.

According to still further features in the described preferred embodiments the cells are of an organism suffering from a condition associated with over production of oxidants.

According to still further features in the described preferred embodiments the organism is a human being and the condition is selected from the group consisting of acute respiratory distress syndrome, amyotrophic lateral sclerosis, atheroscierotic cardiovascular disease, multiple organ dysfunction, Parkinson's disease, Alzheimer's disease, basal ganglia degenerative diseases, motoneuron diseases, Scrapie, spongyform encephalopathy and Creutzfeldt-Jakob's disease.

According to further features in preferred embodiments of the invention described below provided is a method of therapeutically or prophylactically treating an individual known to have a central nervous system neurodegenerative disorder associated with oxidative stress, the method comprising the step of administering a pharmaceutical composition to the individual, the pharmacological composition including a compound, the compound having (a) a combination of molecular weight and membrane miscibility properties for permitting the compound to cross the blood brain barrier of the individual; (b) a readily oxidizable chemical group for exerting antioxidation properties; and (c) a chemical make-up for permitting the compound or its intracellular derivative to accumulate within brain cells of the individual.

According to still further features in the described preferred embodiments the central nervous system neurodegenerative disorder associated with oxidative stress is selected from the group consisting of Parkinson's disease, Alzheimer's disease, basal ganglia degenerative diseases, motoneuron diseases, Scrapie, spongyform encephalopathy and Creutzfeldt-Jakob's disease.

According to still further features in the described preferred embodiments the pharmacological composition further includes a pharmacological carrier.

According to still further features in the described preferred embodiments the pharmacological carrier is selected from the group consisting of a thickener, a carrier, a buffer, a diluent, a surface active agent and a preservatives.

According to still further features in the described preferred embodiments the administration is peripheral.

According to still further features in the described preferred embodiments the peripheral administration is selected from the group consisting of topical administration, oral administration, administration by inhalation, and parenteral administration.

According to further features in preferred embodiments of the invention described below provided is a pharmaceutical composition for reducing or abolishing, extracellular or intracellular, natural or induced oxidation effects imposed on cells of an individual, the composition comprising a compound selected from the group consisting of N-acetyl cysteine ethyl ester, β,β-dimethyl cysteine ethyl ester, N-acetyl-β,β-dimethyl cysteine, glutathione ethyl ester, N-acetyl glutathione ethyl ester, N-acetyl glutathione, N-acetyl (α ethyl ester) glutathione, N-acetyl (α ethyl ester) glutathione ethyl ester, N-acetyl glutathione amide, N-acetyl cysteine amide, N-acetyl β,β dimethyl cysteine amide and N-acetyl cysteine glycine amide.

According to further features in preferred embodiments of the invention described below provided is a compound for therapeutically or prophylactically treating an individual known to have a central nervous system neurodegenerative disorder associated with oxidative stress, the compound comprising (a) a combination of molecular weight and membrane miscibility properties for permitting the compound to cross the blood brain barrier of the individual; (b) a readily oxidizable chemical group for exerting antioxidation properties; and (c) a chemical make-up for permitting the compound or its intracellular derivative to accumulate within brain cells of the individual.

According to still further features in the described preferred embodiments the cells are of an organism suffering from a condition associated with over production of oxidants.

According to still further features in the described preferred embodiments the organism is a human being and the condition is selected from the group consisting of acute respiratory distress syndrome, amyotrophic lateral sclerosis, atheroscierotic cardiovascular disease, multiple organ dysfunction, Parkinson's disease, Alzheimer's disease, basal ganglia degenerative diseases, motoneuron diseases, Scrapie, spongyform encephalopathy and Creutzfeldt-Jakob's disease.

According to further features in preferred embodiments of the invention described below provided is a pharmaceutical composition for therapeutically or prophylactically treating an individual known to have a central nervous system neurodegenerative disorder associated with oxidative stress, the composition comprising a compound, the compound having (a) a combination of molecular weight and membrane miscibility properties for permitting the compound to cross the blood brain barrier of the individual; (b) a readily oxidizable chemical group for exerting antioxidation properties; and (c) a chemical make-up for permitting the compound or its intracellular derivative to accumulate within brain cells of the individual.

The present invention successfully addresses the shortcomings of the presently known configurations by providing compounds, pharmaceutical compositions containing the compounds, methods of preparing the compounds and of using the compounds for therapeutic and prophylactic treatments of oxidative stress associated central nervous system neurodegenerative disorders and other etiologies, which at present have no known adequate treatment.

It is one object of the invention to provide novel antioxidant compounds.

It is another object of the invention to provide novel blood brain barrier crossing antioxidant compounds.

It is still another object of the invention to provide pharmaceutical compositions containing the novel compounds.

It is a further object of the invention to provide methods of using antioxidant compounds capable of crossing the blood brain barrier for therapeutic or prophylactic treatment of central nervous system neurodegenerative disorders.

It is still a further object of the invention to provide a method for treating cells subjected to extracellular or intracellular oxidative stress in both central nervous system neurodegenerative disorders and in disorders of peripheral tissues.

These and other objects of the invention are further delineated hereinbelow.

BRIEF DESCRIPTION OF THE DRAWINGS

The invention herein described, by way of example only, with reference to the accompanying drawings, wherein.

DESCRIPTION OF THE PREFERRED EMBODIMENTS

Figure 1:
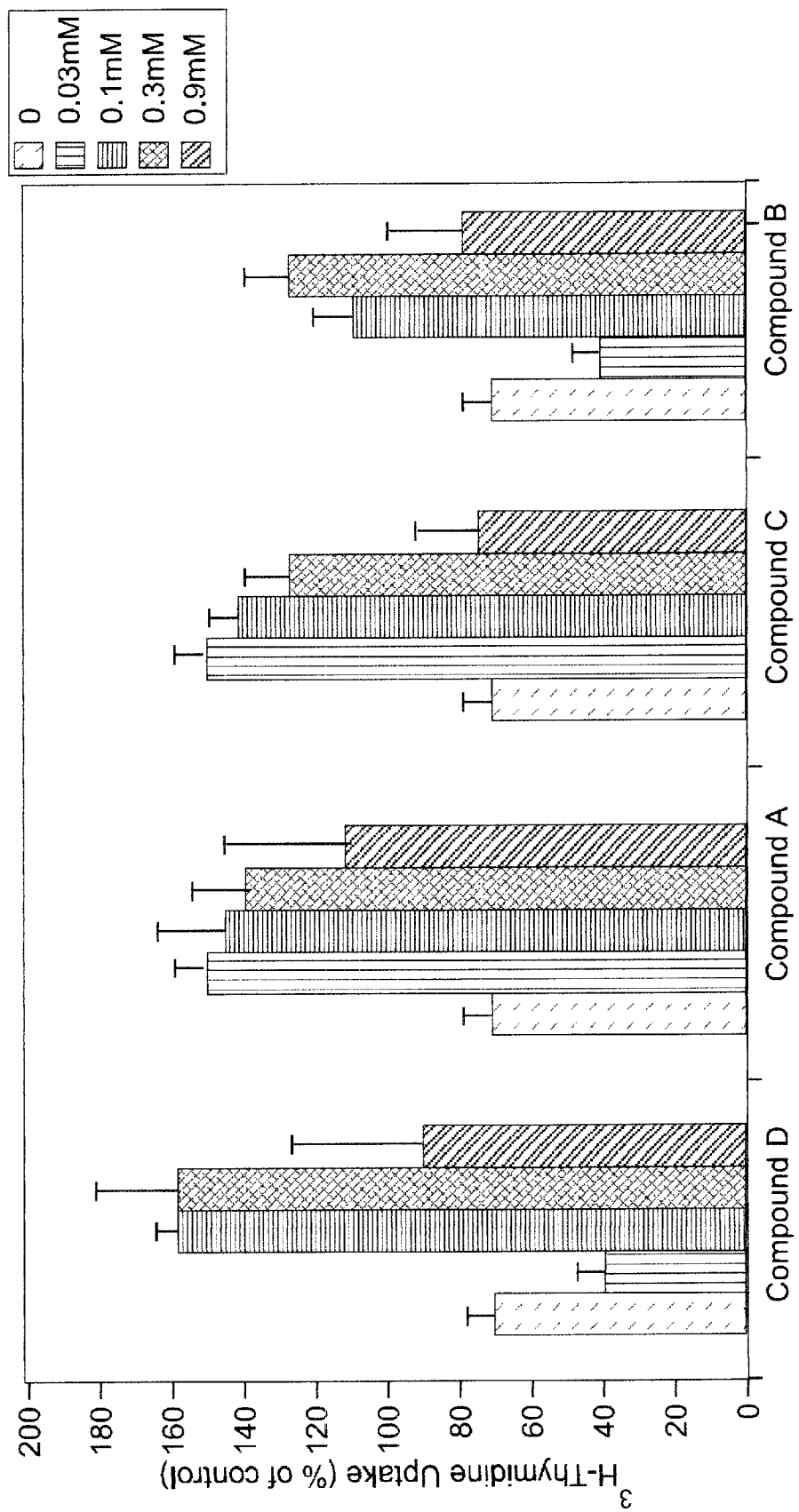
FIG. 1 presents [$^3$H]-thymidine uptake by PC12 cells treated in vitro with 0.5 mM dopamine which confers extracellular oxidative stress by forming oxidation products during its oxidation in the medium rescued with various concentrations of compounds A–D.

The present invention is of composition and use of antioxidant compounds. Specifically, the compounds of the present invention are low molecular weight, hydrophobic antioxidants which can be used for treatment of various etiologies.

More specifically, the compounds of the present invention can be used for treatment of neurodegenerative disorders, in which disorders pathology in the brain is associated with oxidative stress and for treatment of peripheral tissues in conditions associated with overproduction of oxidants.

Thus, the compounds according to the present invention can be used to treat central nervous system neurodegenerative disorders such as, but not limited to, Parkinson's, Alzheimer's and Creutzfeldt-Jakob's diseases, and peripheral tissue disorders such as, but not limited to, acute respiratory distress syndrome, amyotrophic lateral sclerosis, atherosclerotic cardiovascular disease and multiple organ dysfunction, all of which were previously shown to be associated with formation and/or overproduction of oxidants.

The principles of operation of the compounds according to the present invention may be better understood with reference to the drawings and accompanying descriptions.

Antioxidant compounds are used according to the present invention to relieve oxidation stress within cells. Preferred compounds which are used to relieve oxidation stress according to the present invention (i) has a combination of molecular weight and membrane miscibility properties rendering it capable of crossing the blood brain barrier; (ii) includes a readily oxidizable (i.e., reduced) chemical group, such as, but not limited to, a sulfhydryl (—SH) group, for exerting its antioxidation properties and (iii) has a chemical make-up for permitting it or its cellular derivative(s) to accumulate within the cytoplasm of cells, such as brain cells. Collectively, these properties render the compounds suitable for treatment of neurodegenerative disorder of the central nervous system.

Yet, these compounds are also suitable for treating conditions in which peripheral tissues, such as, but not limited to, the lungs and/or heart, are damaged due to overproduction of oxidants (i.e., reactive oxygen species), which is the case in, for example, acute respiratory distress syndrome, amyotrophic lateral sclerosis, atheroscierotic cardiovascular disease and multiple organ dysfunction.

Compounds which have the above listed properties are for example:

(i) N-acetyl cysteine ethyl ester—$C_7H_{11}NO_3S$— of a formula (compound A):

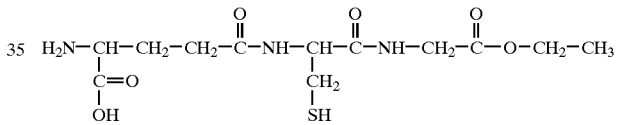

(ii) β,β-dimethyl cysteine ethyl ester or N-acetyl-penicillamine ethyl ester—$C_9H_{18}NO_3S$— of a formula (compound B):

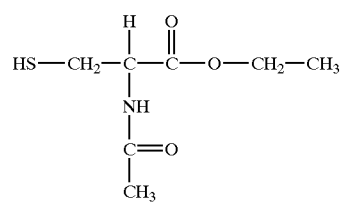

(iii) N-acetyl-β,β-dimethyl cysteine or N-acetyl-penicillamine—$C_7H_{13}NO_3S$— of a formula (compound C):

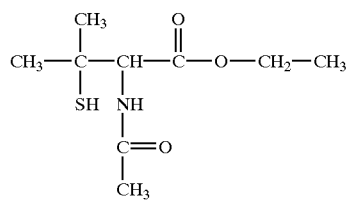

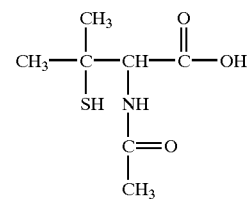

(iv) Glutathione ethyl ester —$C_{12}H_{21}N_3O_6S$— of a formula (compound D):

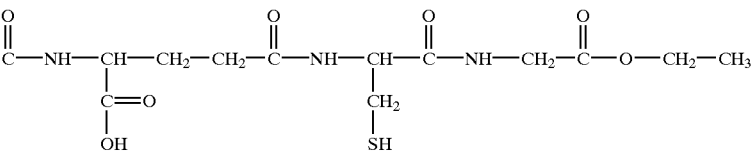

(v) N-acetyl glutathione ethyl ester —$C_{14}H_{23}N_3O_7S$— of a formula (compound E):

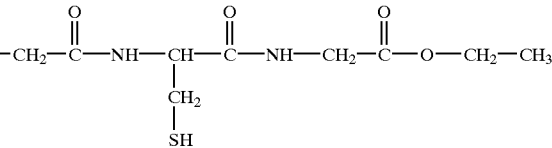

(vi) N-acetyl glutathione —$C_{12}H_{19}N_3O_7S$— of a formula (compound F):

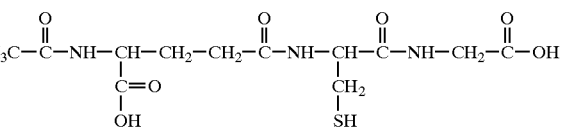

(vii) N-acetyl α-glutamyl ethyl ester cysteinyl glycyl ethyl ester or N-acetyl (β-ethyl ester) glutathione ethyl ester —$C_{16}H_{27}N_3O_7S$— of a formula (compound G):

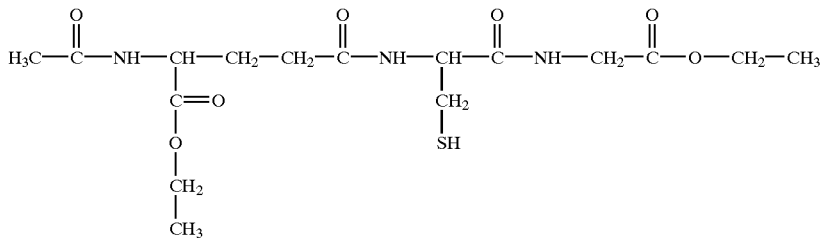

(viii) N-acetyl β-glutamyl ethyl ester cysteinyl glycyl or N-acetyl (β-ethyl ster) glutathione —$C_{14}H_{23}N_3O_7S$— of a formula (compound H):

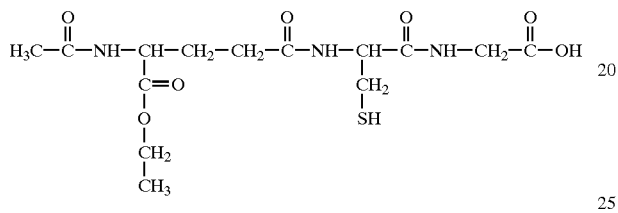

Additional compounds which may serve as antioxidants according to the present invention are:

(ix) N-acetyl glutathione amide —$C_{12}H_{21}N_5O_5S$— of a formula (compound I):

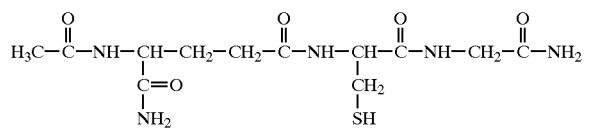

(x) N-acetyl cysteine amide —$C_5H_{10}N_2O_2S$— of a formula (compound J):

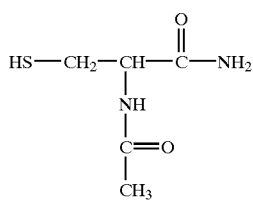

(xi) N-acetyl β,β dimethyl cysteine amide —$C_7H_{15}N_2O_2S$— of a formula (compound K):

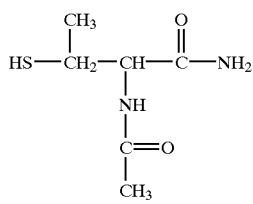

(xii) N-acetyl cysteine glycine amide —$C_7H_{12}N_3O_3S$— of a formula (compound L):

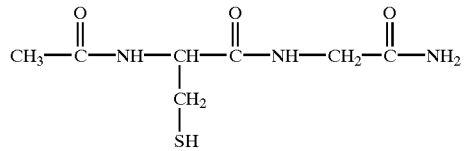

These compounds are used according to the invention as antioxidants which cross the blood brain barrier, for relieving oxidative stress, a common propagator of many neurodegenerative diseases. However, it will be appreciated by one ordinarily skilled in the art, that compounds having the above listed properties may also be used as antioxidants in other etiologies caused by oxidation processes in for example peripheral tissues, i.e., tissues other than central nervous system tissues. According to a preferred embodiment of the invention, the compound is a pro-drug which penetrates the cells due to its solubility in the cell membrane and is hydrolyzed once inside the cell, exerting a drug having the antioxidant activity.

For example compounds A, B, D, E, G and H above are pro-drug compounds.

Compounds A, B, E, G and H above are novel pro-drug compounds, and their hydrolytic products ethanol and N-acetyl-cysteine (for compound A); ethanol and N-acetyl-penicillamine (for compound B); ethanol and N-acetyl glutathione (for compounds E, G and H) are known not to be toxic. The lethal dose 50% (LD50) value for N-acetyl-cysteine is 5,050 mg/kg. N-acetyl-penicillamine is available as an oral medication distributed under the generic name cuprimine by various manufacturers. Whereas N-acetyl glutathione and ethanol are both well known to be non-toxic substances.

A pro-drug according to the invention includes at least one ester moiety such as an alkyl ester or an aryl ester, e.g., methyl ester, ethyl ester, hydroxyethyl ester, t-butyl ester, cholesteryl ester, isopropyl ester and glyceryl ester. Preferably the pro-drug includes an ethyl ester moiety which, on one hand, neutralizes the charge of the carboxylic group(s) and on the other hand, when hydrolyzed within the cells release ethanol which is a substance known not to be toxic to the cells.

Upon entering the cytoplasm of a cell, the pro-drug is de-esterified by one or various intracellular esterases, to release the drug which has at least one carboxyl moiety (—COOH) and a by-product (typically ethanol) which contains the hydroxyl moiety (—OH). The carboxylic group(s) of the drug is typically negatively charged and the drug therefore is trapped within the cell, where it is to exert its antioxidative properties.

Further according to the invention there is provided a method for preparing compounds A and B. The method includes the following steps. First, N-acetyl cysteine (for compound A) or N-acetyl β,β-dimethyl cysteine (for compound B) is mixed with a cooled solution of thionyl chloride and absolute ethanol. Second, the mixture is refluxed. And third, the volatiles are removed from the mixture for obtaining a first residue. Preferably the method further includes the following step. Fourth, the first residue is dissolved in water. And fifth, the first residue is extracted from the water with methylene chloride. Preferably the method further includes the following step. Sixth, the extract is dried to obtain a second residue. Preferably the method further includes the following step. Seventh, the second residue is crystallized from petroleum ether (for compound A) or from a methanol water solution (for compound B). Further detail concerning the method of preparing compounds A and B are delineated hereinbelow in the Examples section.

Compound C is described in Biochem. Prep. 3, 111 (1953) and in U.S. Pat. Nos. 2,477,148 and 2,496,426, both are incorporated by reference as if fully set forth herein, and was prepared essentially as therein described. As mentioned above, compound C, N-acetyl-penicillamine; is available as an oral medication distributed under the generic name cuprimine by various manufacturers.

Compound D above is commercially available from Sigma Biochemicals, Cat. No. G1404. Compounds D is a pro-drug compound, and its hydrolytic products ethanol and glutathione are well known not to be toxic.

Compounds E, G and H above are novel glutathione derivatives and can be prepared, for example, from commercially available building units for Boc and Fmoc chemistry peptide synthesis, as well known in the art.

Compound F is a glutathione derivative and is described in Levy et al., 1993.

Further according to the invention there is provided a method for preparing compounds I, J and K. The method includes the following steps. First, ammonia gas is bubbled through absolute cooled dry ethanol. Second, N-acetyl glutathione ethyl ester (compound G, for synthesis of compound I), N-acetyl cysteine ethyl ester (compound A, for synthesis of compound J) or N-acetyl β,β dimethyl cysteine ethyl ester (compound B, for synthesis of compound K) is added to the ethanol solution. Third, a container holding the reaction is sealed. Fourth, access ammonia and ethanol are evaporated and finally the resulting product is lyophilized. Further detail concerning the method of preparing compounds I, J and K are delineated hereinbelow in the Examples section.

Further according to the invention there is provided a method for preparing compound L which is further detailed in the Examples section that follows.

Any of the glutathione derived compounds (D–H and I) according to the invention may be prepared employing Boc and Fmoc chemistry for peptide synthesis. This, in turn, permits the inclusion of native Levo (L isomer) and/or non-native Dextro (D isomer) glutamic acid and/or cysteine derivatives or residues within any of these compounds. It will be appreciated that by replacing the native L configuration by the non-native D configuration, a compound becomes less recognizable by many enzymes and its biological half life within the body therefore increases. Compounds A–C and J–K also include chiral carbons. Any of these carbons may also acquire a D or an L isomreric configuration.

Thus, compounds A–L above were given chemical names according to all L isomer configurations, i.e., all of their chiral carbon atoms are L isomers. However, as used herein in the specification and in the claims, these chemical names also refer to any of their D isomer(s) containing chiral atoms.

As mentioned above, compounds D–H are glutathione derivatives. These compounds and similar glutathione derivative compounds are represented by the general formula:

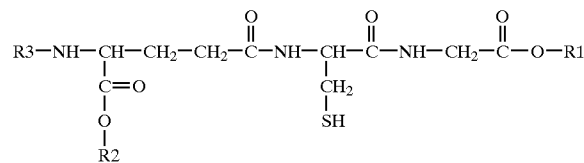

R1 is selected from the group consisting of a hydrogen atom and an alkyl (e.g., $C_1$–$C_{20}$) or aryl (e.g., $C_6$–$C_9$) group. Preferably R1 is an ethyl group.

R2 is selected from the group consisting of a hydrogen atom and an alkyl (e.g., $C_1$–$C_{20}$) or aryl (e.g., $C_6$–$C_9$) group. Preferably R2 is a ethyl group.

Whereas, R3 is selected from the group consisting of a hydrogen atom and an R4-CO (acyl) group, wherein R4 is an alkyl (e.g., $C_1$–$C_{20}$) or aryl (e.g., $C_6$–$C_9$) group. Preferably R4 is a methyl group. However, any one of R1, R2 and R4 can independently be a methyl, ethyl, hydroxyethyl, t-butyl, cholesteryl, isopropyl or glyceryl group.

Compounds A, B and E–L are novel compounds. These compounds are not listed in the Chemical Abstract.

For therapeutic or prophylactic treatment of diseases, disorders or medical conditions, the antioxidant compounds of the present invention can be formulated in a pharmaceutical composition, which may include thickeners, carriers, buffers, diluents, surface active agents, preservatives, and the like, all as well known in the art. Pharmaceutical compositions may also include one or more active ingredients such as but not limited to antiinflammatory agents, antimicrobial agents, anesthetics and the like in addition to the antioxidant compounds.

The pharmaceutical composition may be administered in either one or more of ways depending on whether local or systemic treatment is of choice, and on the area to be treated. Administration may be done topically (including ophtalmically, vaginally, rectally, intranasally), orally, by inhalation, or parenterally, for example by intravenous drip or intraperitoneal, subcutaneous, intramuscular or intravenous injection.

Formulations for topical administration may include but are not limited to lotions, ointments, gels, creams, suppositories, drops, liquids, sprays and powders. Conventional pharmaceutical carriers, aqueous, powder or oily bases, thickeners and the like may be necessary or desirable.

Compositions for oral administration include powders or granules, suspensions or solutions in water or non-aqueous media, sachets, capsules or tablets. Thickeners, diluents, flavorings, dispersing aids, emulsifiers or binders may be desirable.

Formulations for parenteral administration may include, but are not limited to, sterile solutions which may also contain buffers, diluents and other suitable additives.

Dosing is dependent on severity and responsiveness of the condition to be treated, but will normally be one or more doses per day, with course of treatment lasting from several days to several months or until a cure is effected or a diminution of disease state is achieved. Persons ordinarily skilled in the art can easily determine optimum dosages, dosing methodologies and repetition rates.

Reference in now made to the following examples, which together with the above descriptions, illustrate the invention.

EXAMPLE 1

Synthesis of N-acetyl Cysteine Ethyl Ester (Compound A)

N-acetyl cysteine (4.6 mmol) was added in portions to a cooled (e.g., 2–8° C.) solution of 2 ml thionyl chloride and 10 ml absolute ethanol. The resulting mixture was refluxed at 40° C. for 1 hour and then the volatiles were removed in vacuo. The residue was dissolved in 10 ml of water and was extracted twice with 20 ml of methylene chloride. The extract was dried under vacuo. The title compound was crystallized from petroleum ether (fraction 40–60°) in 55% yield.

The resulting product has the following characteristics:
(a) Melting point of 90° C.
(b) Anal. calculated for $C_7H_{11}NO_3S$:

| Calculated: | C, 43.9 | H, 6.8 |
| --- | --- | --- |
| Found: | C, 42.5 | H, 6.0 |

(c) Thin layer chromatography in n-butanol/acetic acid/water (4/1/4): was carried out and the Rf value was Rf=0.91. The Rf value of the reactant, N-acetyl cysteine is 0.78.
(d) Nuclear Magnetic Resonance (NMR) in deutarated trichloromethane (CDC13):
6.51, 0.7H
4.85, 1H, m
4.23, 2H, q, J=7.0
3.44, 0.4H, d, J=4.4
3.22, 2H, t, J=4.4
2.06, 3H, S
1.30, 3H, t, J=7.0

EXAMPLE 2

Synthesis of N-acetyl β,β-dimethyl Cysteine Ethyl Ester or N-acetyl-penicillamine Ethyl Ester (Compound B)

N-acetyl β,β-dimethyl cysteine (2.6 mmol) was added in portions to a cooled (2–8° C.) solution of 2 ml thionyl chloride and 10 ml absolute ethanol. The resulting mixture was refluxed at 40° C. for 1 hour and then the volatiles were removed in vacuo. The residue was dissolved in 10 ml of water and was extracted twice with 20 ml of methylene chloride. The extract was dried under vacuo. The title compound was crystallized from a methanol-water solution (1/100, fraction 40–60°) in 25% yield.

The resulting product has the following characteristics:
(a) Melting point of 180° C.
(b) Thin layer chromatography in n-butanol/acetic acid/water (4/1/4) was carried out and the Rf value was Rf=0.66. The Rf value of the reactant, N-acetyl β,β-dimethyl cysteine is 0.88.
(c) Nuclear Magnetic Resonance (NMR) in deutarated acetone ($D_6$)
4.79, 1 H, d, J=6.0
4.17, 2H, q, J=7.0
2.81, 1H, d, J=6.0
1.98, 3H, S
35: 1.44, 6H, S
1.27, 3H

EXAMPLE 3

Synthesis of N-acetyl Glutathione Amide (compound I)

Ammonia gas was bubbled through absolute dry ethanol at −70° C. (dry ice with acetone), for 10 minutes. N-acetyl glutathione ethyl ester (compound G), 350 mg (1 mmol) was added to the cooled ethanol/ammonia solution and ammonia was continued to bubble through the solution for additional 10 minutes. Then, the solution was corked and was left at room temperature. After 16 hours, the flask was opened and access of ammonia and the ethanol were evaporated under reduced pressure. The product was lyophilized. The yield was 84%.

The resulting product has the following characteristics:
(a) Thin layer chromatography in n-butanol/acetic acid/water (4/1/4) was carried out and the Rf value was Rf=0.71.

EXAMPLE 4

Synthesis of N-acetyl Cysteine Amide (Compound J)

Ammonia gas was bubbled through absolute dry ethanol at −70° C. (dry ice with acetone), for 10 minutes. N-acetyl cysteine ethyl ester (compound A), 163 mg (1 mmol) was added to the cooled ethanol/ammonia solution and ammonia was continued to bubble through the solution for additional 10 minutes. Then, the solution was corked and was left at room temperature. After 16 hours, the flask was opened and access of ammonia and the ethanol were evaporated under reduced pressure. The product was lyophilized. The yield was 98%.

The resulting product has the following characteristics:
(a) Thin layer chromatography in n-butanol/acetic acid/water (4/1/4) was carried out and the Rf value was Rf=0.70. The Rf value of the reactant, N-acetyl cysteine ethyl ester is 0.91.

Alternatively, a solution of 20% piperidine (4 ml) in 16 ml DMF was added to Fmoc Rink amide AM resin (2 gram; 1.1 mmole amide) and the reaction was allowed to proceed for 30 minutes. Ac-S-trityl cysteine (1.3 gram, 3.3 mmole) was added with TBTU (1.06 gram) followed by diisopropyl ethyl amine (1.12 ml). The reaction was carried out for 2 hours. The resin was washed with methylene chloride (×6), and then a mixture of 1 ml silan/0.5 ml water/19 ml of TFA was added. After 1 hour the resin was filtered washed with TFA and solvent evporated. The product was dissolved in water and extracted with methylene choride. The aqueous solution was thereafter lyophyllized.

The resulting product has the following characteristics:
(a) Nuclear Magnetic Resonance (NMR)
4.45 t,1,j=6.96 Hz
2.81 ABX system, $J_{AB}$=12.69, $J_{AX}$+$J_{BX}$=12.45Hz
2.00 s 3Hz

EXAMPLE 5

Synthesis of N-acetyl β,β Dimethtyl Cysteine Amide (Compound K)

Ammonia gas was bubbled through absolute dry ethanol at −70° C. (dry ice with acetone), for 10 minutes. N-acetyl β,β dimethyl cysteine ethyl ester (compound B), 194 mg (1 mmol) was added to the cooled ethanol/ammonia solution and ammonia was continued to bubble through the solution for additional 10 minutes. Then, the solution was corked and was left at room temperature. After 16 hours, the flask was opened and access of ammonia and the ethanol were evaporated under reduced pressure. The product was lyophilized. The yield was 90%.

The resulting product has the following characteristics:
(a) Thin layer chromatography in n-butanol/acetic acid/water (4/1/4) was carried out and the Rf value was Rf=0.50. The Rf value of the reactant, N-acetyl β,β dimethyl cysteine ethyl ester is 0.66.

EXAMPLE 6

Synthesis of N-acetyl Cysteine Glycine Amide
(Compound L)

A solution of 20% piperidine (4 ml) in 16 ml DMF was added to Fmoc Rink glycine amide AM resin (1.1 mmole amide) and the reaction was allowed to proceed for 30 minutes. Ac-S-trityl cysteine (1.3 gram, 3.3 mmole) was then added with TBTU (1.06 gram) followed by diisopropyl ethyl amine (1.12 ml). The reaction was carried out for 2 hours. The resin was washed with methylene chloride (×6), and then a mixture of 1 ml silan/0.5 ml water/19 ml TFA was added.

After 1 hour the resin was filtered washed with TFA and solvents were evaporated.

The product was dissolved in water and extracted with methylene chloride. The aqueous solution was lyophilized.

EXAMPLE 7

In Vitro Extracellular Antioxidation by Compounds A–D

Compounds A–D were assayed in vitro for their extracellular antioxidant activities. The assays were carried out with PC12 cells (Offen et al,. 1996) subjected to a high dose of dopamine which confers oxidative stress to these cells by forming oxidation products during its oxidation in the growth medium, i.e., extracellularly.

With reference now to FIG. 1. To this end, PC12 cells were subjected to high concentration of dopamine (0.5 mM) for 24 hours in the presence of increasing concentrations (0 mM, 0.03 mM, 0.1 nM, 0.3 mM and 0.9 mM) of the various compounds A–D. [$^3$H]-thymidine was added to the cells (1 μCi/100,000 cells) six hours before the end of the 24 hours period. Due to the high lipophylicity of compounds A–D, the compounds were first dissolved in dimethyl sulfoxide (DMSO) and then in water and were applied to the cells in a final concentration of 3% DMSO. The effect of 3% DMSO on the cells was tested separately and the values presented in FIG. 1 are after the appropriate corrections. [$^3$H]-thymidine uptake was measured in triplicate wells containing cells pretreated with dopamine alone and dopamine with each of compounds A–D at the concentrations as indicated above. The results presented in FIG. 1 show the mean of triplicate wells taken from three independent cell batches, wherein control represent cells treated only with 3% DMSO and is defined as 100% [$^3$H]-thymidine uptake (not shown).

Please note that all compounds A–D increased [$^3$H]-thymidine uptake at least at one concentration value. Increase varied between Ca. 1.5 (compound B at 0.03 mM) to Ca. 2.5 (compound D at 0.03 mM and 0.1 mM). Thus, all four compounds showed high potency as protective extracellular antioxidants. Furthermore, some also reversed the basal cellular oxidation state which occurs spontaneously in control cells (not shown). Thus compounds A–D were proven useful as extracellular antioxidants.

EXAMPLE 8

In Vitro Intracellular Antioxidation by Compounds A–D

One of the main characteristics of the oxidative effects in PC12 cells are mimicked by 6-hydroxy-dopamine which is a false neurotransmitter taken up by the cells. Therefore, 6-hydroxy-dopamine was used as another oxidative agent and tested the protective antioxidant efficiencies of compounds A–D within the cells.

Figure 2:
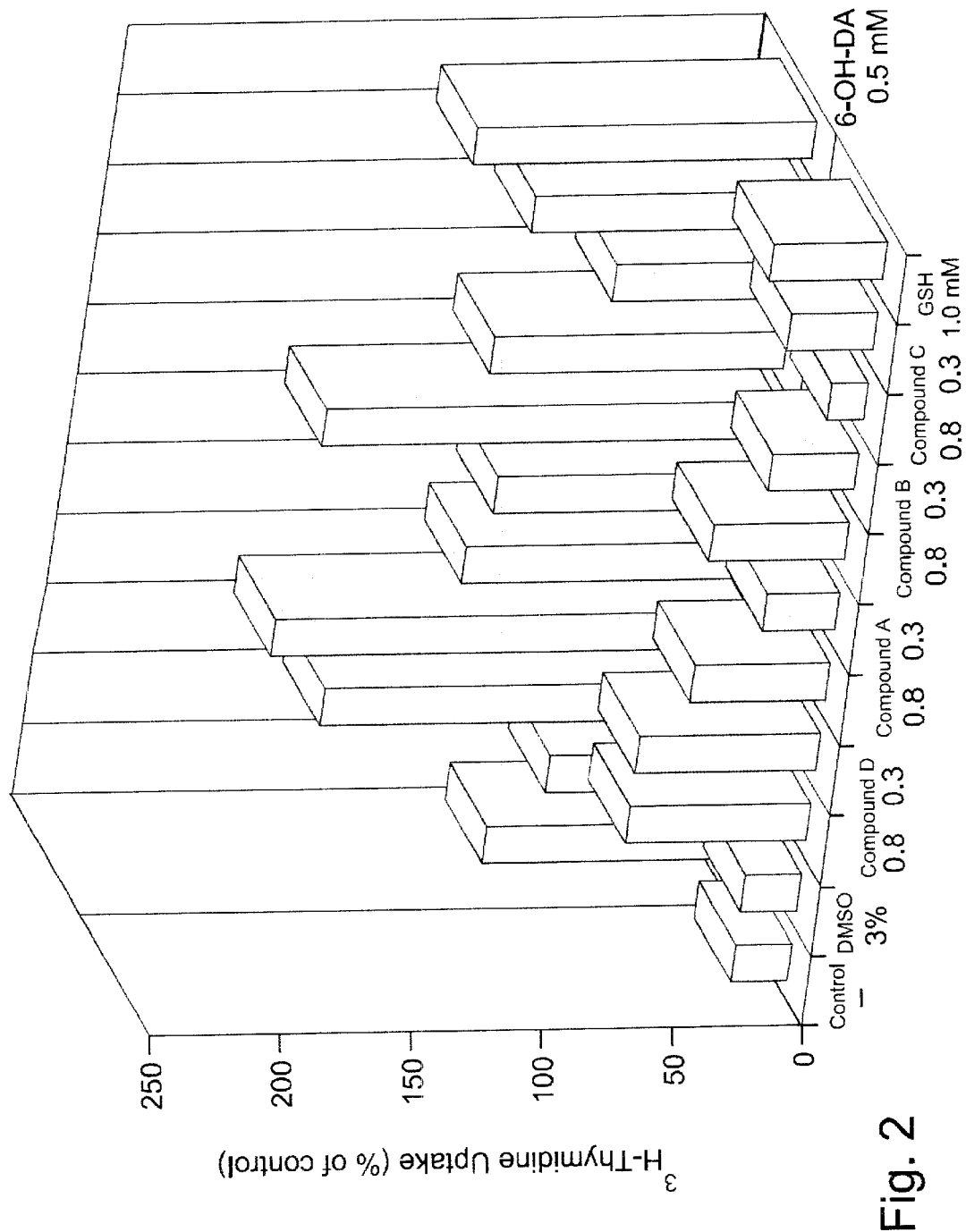
FIG. 2 presents [$^3$H]-thymidine uptake by PC12 cells treated in vitro with 0.5 mM 6-hydroxy-dopamine, which confers intracellular oxidative stress by first entering the cytoplasm and then forming oxidation products during its oxidation in the cytoplasm, protected with various concentrations of compounds A–D and exogenous reduced glutathione (GSH)

With reference now to FIG. 2. To this end, PC12 cells were subjected to high concentration (0.5 mM) of 6-hydroxy-dopamine (6-HO-DA) for 24 hour, in the presence of 0.3 mM or 0.8 mM of compounds A–D or 1 nM of reduced glutathione (GSH) a natural antioxidant, as shown in the front row of FIG. 2. A similar set of cells was treated with the same concentrations of compounds A–D and of reduced glutathione, yet without 6-hydroxy-dopamine, as shown in the back row of FIG. 2. Due to the high lipophylicity of the antioxidants used, they were first dissolved in dimethyl sulfoxide (DMSO), then in water and were applied to the cells in a final concentration of 3% DMSO. [$^3$H]-thymidine was added to the cells (1 μCi/100,000 cells) six hours prior to the end of the 24 hour period.

The results presented in FIG. 2 are the mean of triplicate wells taken from three independent cell batches, wherein control represent un-treated cells and is defined as 100% [$^3$H]-thymidine uptake. The effect of DMSO on the cells was tested separately as shown.

Please note that all compounds A–D increased [$^3$H]-thymidine uptake of 6-hydroxy-dopamine treated cells, at least at one concentration value. Increase varied between Ca. 1.5 (compound C at 0.3 mM) to Ca. 3.5 (compound D at 0.3 mM and 0.8 mM). Thus, all four compounds showed high potency as protective intracellular antioxidants. Furthermore, some also reversed the basal cellular oxidation state which occurs spontaneously in cells not treated with 6-hydroxy-dopamine (FIG. 1, back row). Thus compounds A–D were proven useful as intracellular antioxidants.

EXAMPLE 9

In Vivo Antioxidation by Compounds A–D

To demonstrate that indeed compounds A–D cross the blood brain barrier and affect oxidation state of brain cells, animals were injected with compound A and the endogenous reduced glutathione (GSH) amounts in the serum, in the corpus striatum (at the central nervous system) and/or in the whole brain were determined to evaluate compound A's antioxidation activity within the brain, as was determined by the ratio between endogenous brain (corpus striatum) GSH and endogenous serum GSH.

Figure 3:
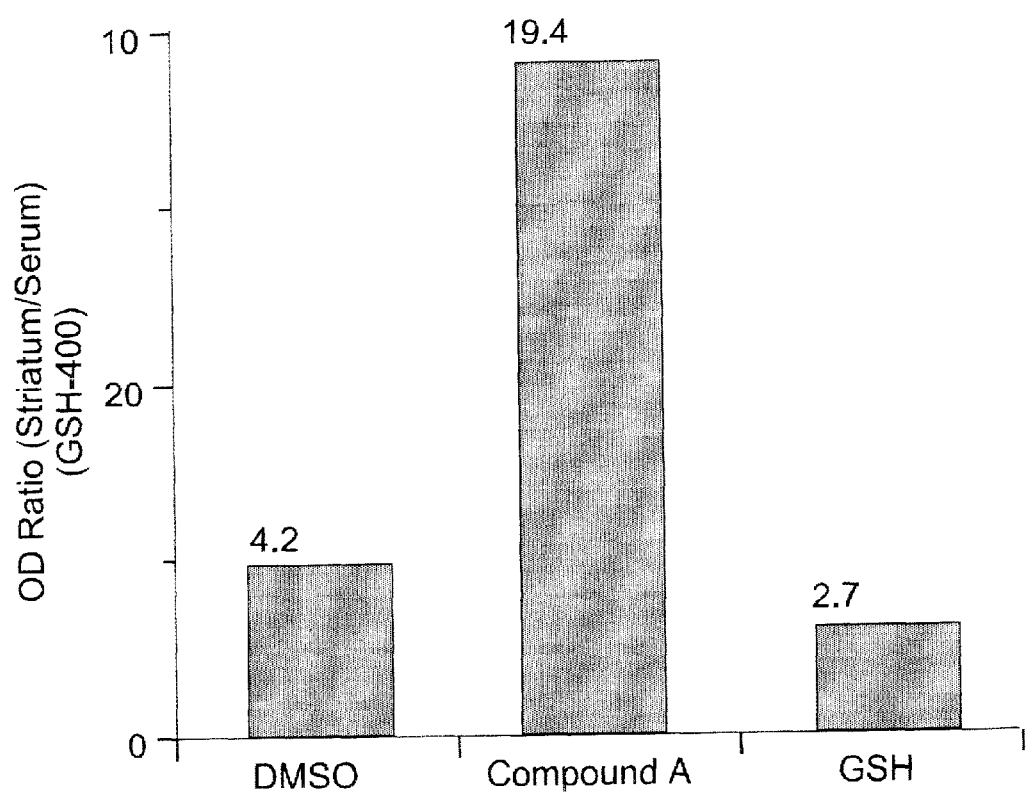
FIG. 3 presents the ratio of endogenous reduced glutathione levels in striatum/serum in two mice injected with 100 mg/kg of compound A in 3% DMSO, 100 mg/kg of reduced glutathione in 3% DMSO, and 3% DMSO injected as a control group, wherein the ratio obtained is marked at the top of the columns. The results represent two animals where each striatum taken separately.

With reference now to FIG. 3. To this end, three groups of two months old Balb/c mice containing two animals in each group were injected intraperitonealy (IP) with 100–300 mg/kg body weight of compound A. Blood samples were drawn from the tail three hours post injection and then the animals were sacrificed and either the corpus striatum or the whole brain were removed and analyzed for GSH levels.

GSH levels were determined using the experimental procedures as described hereinbelow and/or the GSH-400 kit (Oxis International, Inc.).

Preparation of brain homogenates. Animals were rapidly killed and exsanguinated to remove excess blood from the brain. The brain of each animal was rinsed in a beaker containing water, lightly blotted to dry and were weighted. The striatums were transferred into a hand-homogenizer tube and each was homogenized using a constant number (e.g., 20) of up and down strokes of the hand-homogenizer pestle. Each of the homogenates was poured into a centrifuge tube and centrifuged for 10,000 ×g for 5 min. The supernatant was used for GSH determination as follows.

GSH Assay. For each measurement, 200 μl of sample were incubated with 20 μl DTNB [5,5' dithio bis(2-nitrobenzoic acid)] for 1 hour in 37° C. Final absorbance was measured at 400 nm. Similar results were obtained using the GSH-400 kit.

The results shown in FIG. 3 are presented as the OD ratio of striatum/serum endogenous GSH levels. Two control mice were injected with dimethylsulfoxide (DMSO), since DMSO was used as vehicle for the injection of compound A. Exogenous GSH was also administered and used as a control for an antioxidant known not to cross the blood brain barrier.

These results demonstrate that compound A injected IP crosses the blood brain barrier and upon entry to cells at the striatum, increases the level of endogenous GSH, demonstrating its potential protection against oxidative stress.

EXAMPLE 10

In Vivo Antioxidation by Compound J

Detection of compound j (referred to in this Example also as CEA) was established using high performance liquid chromatography (HPLC). To this end, CEA was treated with a fluorescent thiolyte reagent (monobromobimane reagent) and analyzed on an HPLC column.

Protection from oxidative stress in vitro: Neuroblastoma SHSY5Y (NB) cells were maintained in Dulbeco's Modified Eagle's Medium (DMEM), supplemented with 8% FCS and 8% horse serum, penicillin (25 μg/ml), streptomycin (25 μg/ml), 2 mM L-glutamine and 400 μg/ml G418 (Gibco/BRL). For protection experiments cells were subcultured (in 2% serum) to poly-L-lysine-coated 96-well microtiter plates (Nunc), 100 μl of $5 \times 10^5$ cells/ml, CEA was applied to the cells in each well and 4 hours later DA, L-dopa (levodopa), 6-OHDA and MPP+were added for 24 hours.

Survival was assayed by adding neutral red (0.34%, Sigma) to cells in DCCM-1 medium (0.1 ml/well, Bet-Haemek) and incubation for 2 hour at 37° C. The cells were then washed with cold PBS containing 10 mM $MgCl_2$ and the dye was dissolved in 50% ethanol in 50% Somerson buffer (70 mM sodium citrate, 30 mM citric acid, 0.1 N HCl). ELISA reader (590 nm) was used to measure the remaining color intensity.

Crossing the blood-brain-barrier: In vivo experiments were carried out on C57BL/6J mice (15 grams) injected IP with compound J. After incubation (15 min, 60 min or 4 hours) the mice were anesthetized with ether and blood samples were drawn. Then mice underwent perfusion with 50 ml of saline, injected into the right ventricle. The levels of compound I in the brain and in the plasma were detected by selective fluorescent labeling using high performance liquid chromatography (HPLC).

Figure 4:
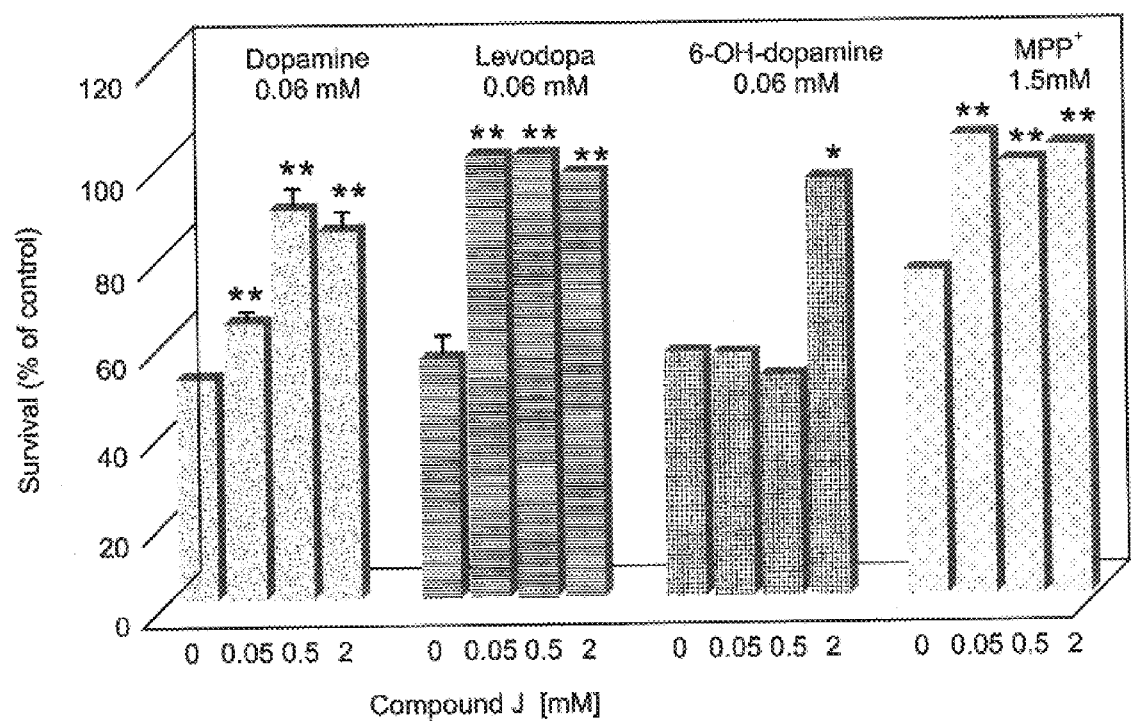
FIG. 4 demonstrates that Compound J at as low as 0.1 mM protect NB cells against the toxicity (>50%) of DA, L-dopa (levodopa), 6-OHDA (0.1–0.25 mM) and MPP$^+$(0.5–2 mM). Cell survival was monitored by the neutral red assays.
Figure 5A:
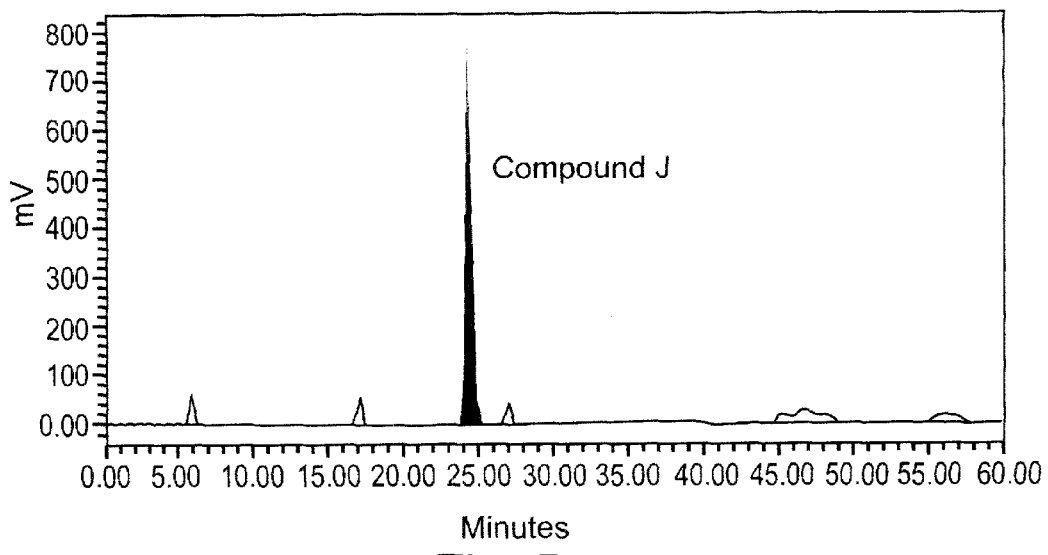
FIG. 5a shows HPLC profile of purified compound J.
Figure 5B:
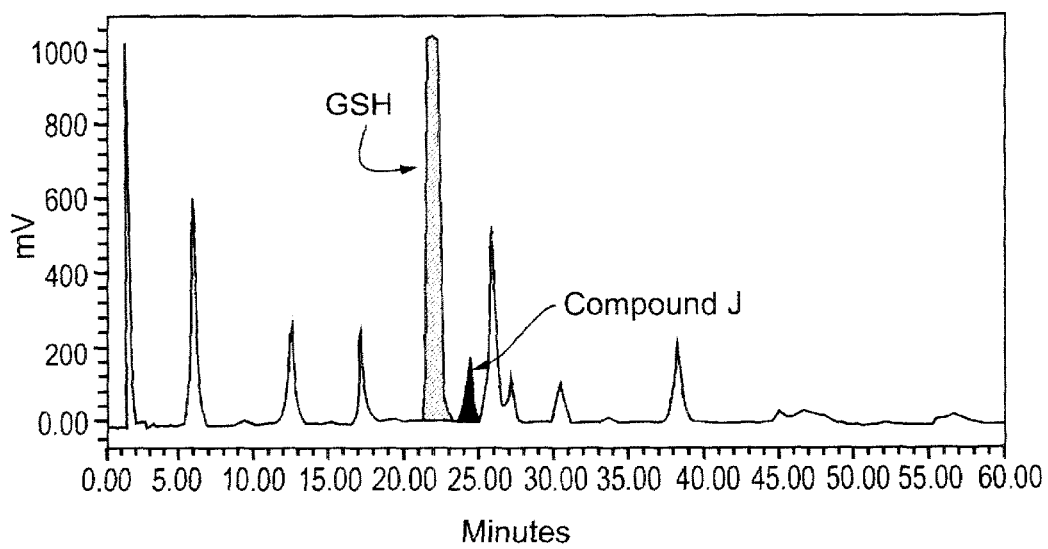
FIG. 5b shows HPLC profile of a brain extract of a mouse 15 minutes following IP injection of compound J.
Figure 6:
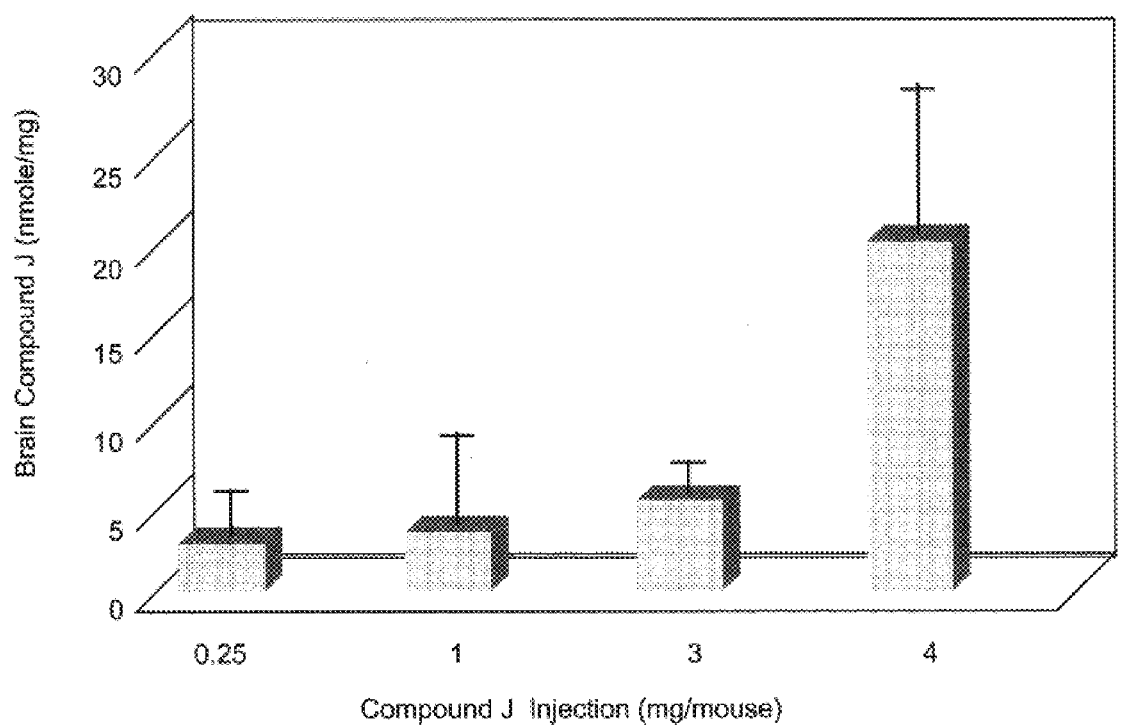
FIG. 6 shows the concentration of compound J in brain extracts of mice 15 minutes following IP injection of compound J at the amounts indicated.

The results are shown in FIGS. 4–6.

Increasing concentrations of compound J were added to NB cells. compound J at 0.1 mM was found to protect the cells against the toxicity (>50%) of DA, L-dopa (levodopa), 6-OHDA (0.1–0.25 mM) and MPP+(0.5–2 mM). Cell survival was increased up to 95% in 0.3 mM compound J as indicated by neutral red assays (FIG. 4).

Increasing amounts of compound J were injected IP and 15 min later, mice were perfused with saline and compound J levels in the brain extracts were determined by HPLC chromatography (FIG. 5b), as compared to a control,. pure, uninjected compound J (FIG. 5a).

IP injection of increasing concentrations (0.25–4 mg) of compound J showed a concentration-dependent increase of compound J in the brain (FIG. 6).

As shown in FIG. 5b, GSH levels were also increased in parallel to compound J presence showing up to 46% increase over untreated animals.

These data indicate that the newly synthesized thiol-substance, compound J, effectively protects cells grown in tissue culture from oxidative stress. It crosses the BBB as shown by the combined fluorescent labeling and HPLC chromatography. Furthermore, it increases endogenous GSH levels in mice brain after IP injection.

While the invention has been described with respect to a limited number of embodiments, it will be appreciated that many variations, modifications and other applications of the invention may be made.

LIST OF REFERENCES IN ALPHABETICAL ORDER

Brown, D. R., Schmidt, B. & Kretzschmar, H. A. Role of microglia and host prion protein in neurotoxicity of a prion protein fragment. Nature 380, 345–347 (1996).

Bundy, G. L., Ayer, D. E., Banitt, L. S., Belonga, K. L., Mizsak, S. A., Palmer, J. R., Tustin, J. M., Chin, J. E., Hall, E. D., Linseman, K. L., et al. Synthesis of novel 2,4-diaminopyrrolo-[2,3-d]pyrimidines with antioxidant, neuroprotective, and anti asthma activity. J Med Chem. 38, 4161–3 (1995).

Cafe, C., Torri, C., Betorelli, L., Angeretti, N., Luccan E., Forloni, G., & Marzatico, F., Oxidative stress after acute and chronic application of b-amyloid fragment 25–35 in cortical cultures. Neuroscience Letts. 203, 61–65 (1996).

Craig. C. Transcend therapeutics takes flight against oxidative stress public. BioWorld Today. Aug. 27, 1996, pp. 1–2.

Fahn S. & Cohen, G. The oxidant stress hypothesis in Parkinson's disease: evidence supporting it. Ann Neurol. 32, 804–812 (1992).

Gash., D. M., Zhang, Z., Ovadia, A., Cass, W. A., Simmermann, A. Y. L., Russell., D., Martin, D., Lapchak, P. A., Collins, F., Hoffer, B. J. & Gerhardt, G. A. Furecovery in parkinsonian monkeys treated with GDNF. Nature, 380 252–255 (1996).

Jenner, O. Oxidative damage in neurodengenerative disease. Lancet, 344, 796–798 (1994).

Levy, E. G., Anderson, M. E. and Meister A. On the synthesis and characterization of N-formylglutathione and N-acetylglutathione. Anal. Biochem., 214, 135–137 (1993).

Offen, D., Ziv, I., Srernin, H., Melamed, E. and Hochman, A. Prevention of dopamine-induced cell death by thiol-antioxidants: Possible implications for treatment of Parkinson's disease. Exptt. Neurol., 141, 32–39 (1996).

Olanow, C. W. A. radical hypothesis for neurodegeneration. Trends. Neurol. Soc. 16, 439–444 (1993).

Olanow, C. W. Oxidation reactions in Parkinson's disease. Neurology 40, 32–37 (1990).

Sian, J., Dexter, D. T., Lees, A. J.,. Daniel, S., Jenner, P & Marsden, C. D. Glutathione-related enzymes in brain in Parkinson's disease. Ann. Neurol. 36, 356–361 (1994).

Spencer, J. P., Jenner, A., Aruoma, O. I., Evans, P. J. Kauer, H., Dexter, D. T., Jenner, P., Lees, A. J., Marsden, D. C. & Haliwell, B. Intense oxidative DNA damage promoted by L-DOPA and its metabolites. FEBS Letts. 353, 246–250 (1994).

The Parkinson Study Group. Effects of tocopherol and deprenyl on the progression of disability in early Parkinson's disease. N. Eng. J. Med. 328, 176–183 (1993).

Thomas, T., Thomas, G. M., McLendon, C., Sutton, T. & Mullan, M. β-Amyloid-mediated vasoactivity and vascular endothelial damage. Nature 380, 168–171 (1996).

What is claimed is:

1. A method of reducing oxidative stress in a tissue of an organism, the method comprising administering to the organism compound (J):

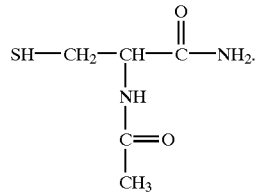

2. The method of claim 1, wherein said organism is a human being suffering from a condition associated with over production of oxidants.

3. The method of claim 2, wherein said condition is selected from the group consisting of acute respiratory distress syndrome, amyotrophic lateral sclerosis, atherosclerotic cardiovascular disease, multiple organ dysfunction, Parkinson's disease, Alzheimer's disease, basal ganglia degenerative diseases, motoneuron diseases, Scrapie, spongyform encephalopathy and Creutzfeldt-Jakob's disease.

4. A method of reducing oxidative stress in the brain of an organism having a blood brain barrier, the method comprising administering to the organism an amide compound (J) having the formula:

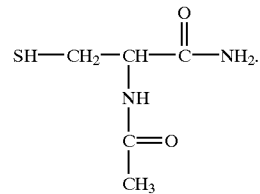

5. The method of claim 4, wherein said administration is systemic.

6. The method of claim 4, wherein said organism is a human being.

7. The method of claim 6, wherein the oxidative stress in the brain is a pathology caused by a neurodegenerative disorder.

8. The method of claim 7, wherein said neurodegenerative disorder is selected from the group consisting of Parkinson's disease, Alzheimer's disease, basal ganglia degenerative diseases, motoneuron diseases, Scrapie, spongyform encephalopathy and Creutzfeldt-Jakob's disease.

* * * * *